(12) United States Patent
Rowe et al.

(10) Patent No.: US 10,363,235 B2
(45) Date of Patent: *Jul. 30, 2019

(54) COMPOSITIONS COMPRISING 15-HEPE AND METHODS OF TREATING OR PREVENTING FIBROSIS USING SAME

(71) Applicant: Afimmune Limited, Dublin (IE)

(72) Inventors: Jonathan Rowe, Waterford, CT (US); Kevin Duffy, Dublin (IE); John Climax, Dublin (IE)

(73) Assignee: Afimmune Limited (IE)

( * ) Notice: Subject to any disclaimer, the term of this patent is extended or adjusted under 35 U.S.C. 154(b) by 0 days.

This patent is subject to a terminal disclaimer.

(21) Appl. No.: 15/062,636

(22) Filed: Mar. 7, 2016

(65) Prior Publication Data

US 2016/0184252 A1 Jun. 30, 2016

Related U.S. Application Data

(63) Continuation of application No. PCT/US2015/063488, filed on Dec. 2, 2015.

(60) Provisional application No. 62/086,535, filed on Dec. 2, 2014.

(51) Int. Cl.
| | |
|---|---|
| *A61K 31/202* | (2006.01) |
| *A61K 31/232* | (2006.01) |
| *A61K 31/557* | (2006.01) |
| *A61K 45/06* | (2006.01) |
| *A61P 1/16* | (2006.01) |
| *A61P 11/00* | (2006.01) |

(52) U.S. Cl.
CPC .......... *A61K 31/202* (2013.01); *A61K 31/232* (2013.01); *A61K 31/557* (2013.01); *A61K 45/06* (2013.01); *A61P 1/16* (2018.01); *A61P 11/00* (2018.01)

(58) Field of Classification Search
CPC .................................................. A61K 31/202
USPC ........................................ 514/560, 549, 547
See application file for complete search history.

(56) References Cited

U.S. PATENT DOCUMENTS

| 8,239,790 | B2 * | 8/2012 | Culp ................... G06F 17/5045 716/51 |
|---|---|---|---|
| 8,293,790 | B2 | 10/2012 | Manku et al. |
| 9,056,086 | B2 * | 6/2015 | Manku ................ A61K 31/202 |
| 9,855,238 | B2 | 1/2018 | Coughlan et al. |
| 2002/0055538 | A1 | 5/2002 | Serhan et al. |
| 2005/0239889 | A1 | 10/2005 | Gosselin |
| 2007/0105954 | A1 | 5/2007 | Puri |
| 2010/0233724 | A1 | 9/2010 | Watkins et al. |
| 2011/0059885 | A1 | 3/2011 | Lea et al. |
| 2011/0105510 | A1 | 5/2011 | Ishikawa |
| 2012/0142773 | A1 | 6/2012 | Kelliher et al. |
| 2012/0213824 | A1 | 8/2012 | Kelliher et al. |
| 2012/0232147 | A1 | 9/2012 | Manku et al. |
| 2012/0264705 | A1 | 10/2012 | Manku et al. |
| 2012/0264824 | A1 | 10/2012 | Mizuguchi et al. |
| 2013/0101533 | A1 | 4/2013 | Manku et al. |
| 2013/0102575 | A1 | 4/2013 | Manku et al. |
| 2013/0267598 | A1 | 10/2013 | Manku et al. |
| 2013/0274338 | A1 | 10/2013 | Manku et al. |
| 2014/0079631 | A1 | 3/2014 | Serhan et al. |

FOREIGN PATENT DOCUMENTS

| EP | 2762143 | 8/2014 |
|---|---|---|
| JP | 2000191525 | 7/2000 |
| JP | 2005179211 | 7/2005 |
| WO | WO 2010/125340 | 11/2010 |
| WO | WO2013057284 | 4/2013 |
| WO | WO2013057287 | 4/2013 |
| WO | WO2013082265 | 6/2013 |
| WO | WO2013112876 | 8/2013 |
| WO | WO2013124479 | 8/2013 |
| WO | WO2013170006 | 11/2013 |
| WO | 2014/118097 A1 | 8/2014 |

OTHER PUBLICATIONS

Flachs et al., "Synergistic induction of lipid catabolism and anti-inflammatory lipids in white fat of dietary obese mice in response to calorie restriction and n-3 fatty acids", 2011, 54:2626-2638.
Ishii et al., "Eicosapentaenoic acid ameliorates steatohepatitis and hepatocellular carcinoma in hepatocyte-specific Pten-deficient mice", Journal of Hepatology, 2009, pp. 562-571.
PCT Application No. PCT/EP2014/051455, International Search Report and Written Opinion, dated Jan. 24, 2014, 10 pages.
PCT Application No. PCT/US2015/63488, International Search Report and Written Opinion, dated Feb. 3, 2016, 9 pages.
GS Masterton et al., "Review article: omega-3 fatty acids—a promising novel therapy for nonalcoholic fatty liver disease," Alimentary Pharmacology & Therapeutics, pp. 679-692, Apr. 30, 2010.
Tanaka et al., "Highly-purified eicosapentaenoic acid treatment improves nonalcoholic steatohepatitis," Journal of Clinical Gastroenterology, Apr. 1, 2008, pp. 413-418.
Barnes, "Mediators of Chronic Obstructive Pulmonary Disease," Pharmacol Rev 56(4):515-48 (Dec. 2004).
Brooks et al., "The fatty acid oxidation product 15-A3t-isoprostane is a potent inhibitor of NFκb transcription and macrophage transformation," Journal of Neurochemistry 119:604-616 (Nov. 2011).
Kajikawa et al., "Eicosapentaenoic acid attenuates progression of hepatic fibrosis with inhibition of reactive oxygen species production in rats fed methionine—and choline-deficient diet," Dig Dis Sci 56(4):1065-74 (Aug. 12, 2010).
Parker et al., "Omega-3 supplementation and non-alcoholic fatty liver disease: a systematic review and meta-analysis," J. Hepatol. 56(4):944-51 (Apr. 2012).
Kendall et al., "Distribution of Bioactive Lipid Mediators in Human Skin," The Journ. of Investigative Dermatology. (2015), 00, 1-11.

(Continued)

*Primary Examiner* — Jennifer M Kim
(74) *Attorney, Agent, or Firm* — Perkins Coie LLP

(57) ABSTRACT

The present disclosure provides compositions comprising 15-HEPE and methods of using same for treating and/or preventing fibrosis in a subject in need thereof.

19 Claims, 13 Drawing Sheets

(56) References Cited

OTHER PUBLICATIONS

Miller et al., "Dietary Supplementation with Ethyl Ester Concentrates of Fish Oil (N-3) and Borage Oil (N-6) Polyunsaturated Fatty Acids Induces Epidermal Generation of Local Putative Anti-Inflammatory Metabolites," The Journ. of Invest. Dermatol., vol. 96, No. 1, pp. 98-103 (1991).

Miller et al., "Guinea Pig Epidermins Generates Putative Anti-Inflammatory Metabolites from Fish Oil Polyunsaturated Acids," Lipids, vol. 24, No. 12 (1989).

PCT Application No. PCT/IB2016/000202, International Search Report and Written Opinion, dated Jun. 6, 2016, 4 pages.

Vang K, et al., "15-lipoxygenase metabolites of gamma-linolenic acid/eicosapentaenoic acid suppress growth and arachidonic acid metabolism in human prostatic adenocarcinoma cells: Possible implications of dietary fatty acids", Prostaglandins Leukotrienes and essential fatty acids, Churchill Lingstone, Edinburgh, vol. 72, No. 5, pp. 363-372 (2005).

Lodish H et al., "Section 5.3 Biomembranes: Structural Organization and Basic Functions," Molecular Cell Biology. 4th Edition. New York. W.H. Freeman. (2000).

Cooper GM, "Structure of the Plasma Membrane," The Cell: A Molecular Approach. 2nd Edition. Sunderland (MA). Sinauer Associates. (2000).

Ishii et al., "Eicosapentaenoic acid ameliorates steatohepatitis and hepatocellular carcinoma in hepatocyte-specific Pten-deficient mice", Journal of Hepatology, 2009, pp. 562-571 (Mar. 1, 2009) (available online Dec. 27, 2008).

Das, "A defect in the activities of $\Delta^6$ and $\Delta^5$ desaturases and pro-resolution bioactive lipids in the pathobiology of non-alcoholic fatty liver disease," World Journal of Diabetes 2(11):176-188 (publication date: Nov. 15, 2011).

International Search Report and Written Opinion dated Mar. 27, 2014 for PCT/EP2014/051455.

Kajikawa et al., "Eicosapentaenoic acid attenuates progression of hepatic fibrosis with inhibition of reactive oxygen species production in rats fed methionine—and choline-deficient diet," Dig Dis Sci 56(4):1065-74 (publication date: Apr. 2011, epublication date: Sep. 17, 2010).

Masterton et al., "Review article: omega-3 fatty acids—a promising novel therapy for non-alcoholic fatty liver disease," Alimentary Pharmacology & Therapeutics, 31(7):679-692 (publication date: Apr. 30, 2010, epublication date: Mar. 1, 2010).

Nguyen et al., "Mechanisms for anti-inflammatory effects of 1-[15(S)-hydroxyeicosapentaenoyl] lysophosphatidylcholine, administered intraperitoneally, in zymosan A-induced peritonitis," British Journal of Pharmacology 162(5):1119-1135 (publication date: Mar. 2011, epublication date: Nov. 22, 2010).

Tanaka et al., "Highly-purified eicosapentaenoic acid treatment improves nonalcoholic steatohepatitis," Journal of Clinical Gastroenterology, 42(4):413-418 (publication date: Apr. 1, 2008).

\* cited by examiner

COMPOSITIONS COMPRISING 15-HEPE AND METHODS OF TREATING OR PREVENTING FIBROSIS USING SAME

PRIORITY CLAIM

This application is a continuation of International Application PCT/US15/63488, with an international filing date of Dec. 2, 2015, which claims priority to U.S. Provisional Patent Application Ser. No. 62/086,535, filed Dec. 2, 2014, the entire contents of each of which are incorporated herein by reference.

FIELD

The present disclosure provides compositions, formulations and methods of treating or preventing fibrosis (e.g., liver fibrosis) by administering a pharmaceutical composition comprising 15-hydroxyeicosapentaenoic acid (also referred to as 15-HEPE or 15-OHEPA) to a subject in need thereof.

BACKGROUND

Fibrosis is characterized by the formation of excess connective tissue in an organ or a tissue. Typically, fibrosis occurs in response to damage to the organ or tissue. Because the process can include crosslinking of connective tissue molecules, effective therapies for reversing fibrosis are few and far between. Although preventative therapies have long been theorized, the fibrosis mechanism has so far proven too complex to conquer. To date, for example, there are no FDA-approved liver fibrosis therapies, and only a handful of proposed therapies have shown promise over the last two decades. See, e.g., Schuppan and Kim, *J. Clin. Invest.*, vol. 123(5), pages 1887-1901 (2013).

Improved therapies for treating and/or preventing fibrosis are therefore needed.

SUMMARY

In some embodiments, the present disclosure provides methods of treating and/or preventing fibrosis in a subject in need thereof, the method comprising administering to the subject a composition comprising 15-HEPE.

In some embodiments, the present disclosure provides methods of treating fibrosis in a subject on fibrosis therapy, the method comprising administering to the subject a composition comprising 15-HEPE.

In some embodiments, the present disclosure provides compositions for treating and/or preventing fibrosis in a subject in need thereof, wherein the compositions comprise an effective amount of 15-HEPE.

In some embodiments, the present disclosure provides uses of 15-HEPE in the manufacture of a medicament for treating and/or preventing fibrosis in a subject.

Other features and advantages of the technology disclosed herein will be apparent from the following detailed description.

DETAILED DESCRIPTION

Figure 1:
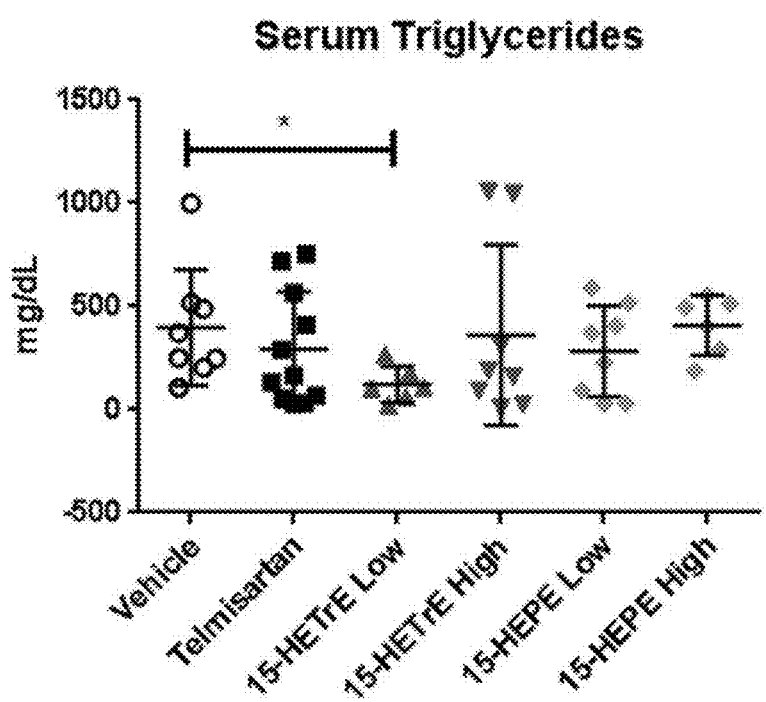
FIG. 1 shows differences in serum triglycerides for mice given a single dose of steptozotocin after birth, fed a high-fat diet for 4 weeks, then treated for 8 weeks with vehicle, telmisartan (2-(4-{[4-Methyl-6-(1-methyl-1H-1,3-benzodiazol-2-yl)-2-propyl-1H-1,3-benzodiazol-1-yl]methyl}phenyl)benzoic acid, also referred to as MICARDIS®), 15-hydroxyeicosa-8(Z),11(Z),13(E)-trienoic acid (15-HETrE), or 15-HEPE.

The present disclosure provides compositions comprising 15-HEPE, and methods of using same for treating and/or preventing fibrosis in a subject in need thereof.

15-Hydroxy-eicosa-5,8,11,13,17-pentaenoic acid is a functionalized fatty acid having the general structure shown in Formula (I).

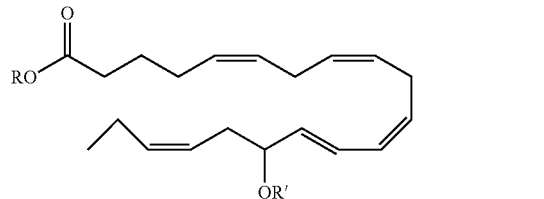

Formula (I)

15-HEPE can be synthesized from eicosapentaenoic acid (EPA) according to methods known in the art. As used herein, the term "15-HEPE" may refer to 15-HEPE in its free acid form (e.g., 15-hydroxy-eicosa-5,8,11,13,17-pentaenoic acid; R=R'=H in Formula (I)) and/or a derivative thereof, such as a pharmaceutically acceptable ester (R≠H), a conjugate, or a salt (R is an ion) consistent with Formula (I), or mixtures of any of the foregoing. A derivative of 15-HEPE (e.g., R≠H and/or R'≠H) may be used instead. In some embodiments, the 15-HEPE is used in the free acid form (i.e., R=H). Alternatively, pharmaceutically acceptable esters or salts of 15-HEPE are used in certain embodiments of the present disclosure. In some embodiments, the 15-HEPE is in the form of a $C_{1-4}$ alkyl ester such as methyl ester (R=$CH_3$) or ethyl ester (R=$CH_2CH_3$) form. 15-HEPE is a chiral molecule and may be used in the 15(S)- or 15(R)-enantiomeric form, in an enantiomerically enriched form, or as a racemic mixture. Used herein, "15-HEPE" includes all such forms, with no limitation as to stereospecificity. In another embodiment, the 15-HEPE comprises the 15(S) form: 15(S)-hydroxy-(5Z,8Z,11Z,13E,17Z)-eicosapentaenoic acid, or a derivative thereof. In some embodiments, the 15-HEPE may be used in the form of the ethyl ester.

As used herein, "EPA" refers to eicosa-5,8,11,14,17-pentaenoic acid, also known as 20:5n-3, an omega-3 fatty acid. EPA is readily obtainable through commercial sources.

Accordingly, in one aspect of the present disclosure, a method of treating and/or preventing fibrosis in a subject is provided, comprising administering to the subject a therapeutically effective amount of a composition comprising 15-HEPE.

The present disclosure provides 15-HEPE, or a composition comprising 15-HEPE, for use in the treatment and/or prevention of fibrosis.

The present disclosure provides a use of 15-HEPE, or a composition comprising 15-HEPE, in the manufacture of a medicament for treating and/or preventing fibrosis.

In another aspect, the present disclosure provides a pharmaceutical composition comprising a therapeutically effective amount of 15-HEPE. The 15-HEPE may be the sole active ingredient (e.g., API) in the pharmaceutical composition and in the methods and uses as stated herein. The 15-HEPE may be the sole active ingredient. Alternatively, the 15-HEPE may be combined for co-formulation or co-administration with another agent or agents for treating and/or preventing fibrosis. If an additional active agent or agents is/are to be used, the 15-HEPE can be co-formulated as a single dosage unit, or the 15-HEPE and the additional fibrosis therapeutic agent can be formulated as two to a plurality of dosage units for coordinated, combination or concomitant administration.

The present disclosure also provides formulations of 15-HEPE and formulations comprising 15-HEPE and methods of using these formulations for treating and/or preventing fibrosis.

The present disclosure further provides a pharmaceutical composition for oral delivery, comprising 15-HEPE. That composition may comprise a pharmaceutically acceptable excipient. The 15-HEPE may be in any form as discussed herein. The 15-HEPE may be present from about 50 mg to about 3000 mg.

15-Hydroxyeicosapentaenoic acid (15-HEPE)

In one embodiment, compositions of the present disclosure comprise 15-HEPE as an active ingredient. 15-HEPE is the abbreviation for 15-hydroxyeicosapentaenoic acid, a metabolite of eicosapentaenoic acid (EPA) that can be synthesized via ways known in the art, such as exposure of eicospentaenoic acid to the enzyme 15-lipoxygenase. As used herein, the term "15-HEPE" refers to 15-HEPE in its free acid form (e.g., 15-hydroxyeicosapentaenoic acid) and/or a pharmaceutically acceptable ester, conjugate or salt thereof, or mixtures of any of the foregoing. A derivative of 15-HEPE may be used instead, though this does not include any derivative compound missing the hydroxy group of 15-HEPE. The term "pharmaceutically acceptable" in the present context means that the substance in question does not produce unacceptable toxicity to the subject or interaction with other components of the composition.

In one embodiment, the 15-HEPE is in the form of an ester (also referred to herein as E-15-HEPE or ethyl-15-HEPE). In another embodiment, the 15-HEPE comprises a $C_1$-$C_5$ alkyl ester of 15-HEPE. In another embodiment, the 15-HEPE comprises 15-HEPE methyl ester, 15-HEPE propyl ester, or 15-HEPE butyl ester. In still another embodiment, the 15-HEPE comprises the optically active 15(S)-Hydroxy-(5Z,8Z,11Z,13E,17Z)-eicosapentaenoic acid. This isomer may be used in any of the forms discussed above.

In another embodiment, the 15-HEPE comprises lithium 15-HEPE, mono-, di- or triglyceride 15-HEPE or any other ester or salt of 15-HEPE, or the free acid form of 15-HEPE.

In various embodiments, the present disclosure provides pharmaceutical compositions, for example orally deliverable compositions, comprising 15-HEPE. In one embodiment, the compositions comprise a therapeutically effective amount of 15-HEPE. In one embodiment, the pharmaceutical composition comprises about 0.1% to about 99%, about 1% to about 95%, about 5% to about 90% by weight of 15-HEPE.

In one embodiment, the pharmaceutical composition comprises about at least about 70%, at least about 80% or at least about 90%, by weight, of 15-HEPE. In one embodiment, the pharmaceutical composition comprises at least about 50%, at least about 60%, at least about 70%, at least about 80% or at least about 90%, by weight of 15-HEPE.

In another embodiment, 15-HEPE is present in a composition of the present disclosure in an amount of about 1 mg to about 10,000 mg, 25 mg to about 7500 mg, about 25 mg to about 5000 mg, about 50 mg to about 5000 mg, about 50 mg to about 3000 mg, about 75 mg to about 2500 mg, or about 100 mg to about 1000 mg, for example about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1025 mg, about 1050 mg, about 1075 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg, about 2500 mg, about 2525 mg, about 2550 mg, about 2575 mg, about 2600 mg, about 2625 mg, about 2650 mg, about 2675 mg, about 2700 mg, about 2725 mg, about 2750 mg, about 2775 mg, about 2800 mg, about 2825 mg, about 2850 mg, about 2875 mg, about 2900 mg, about 2925 mg, about 2950 mg, about 2975 mg, about 3000 mg, about 3025 mg, about 3050 mg, about 3075 mg, about 3100 mg, about 3125 mg, about 3150 mg, about 3175 mg, about 3200 mg, about 3225 mg, about 3250 mg, about 3275 mg, about 3300 mg, about 3325 mg, about 3350 mg, about 3375 mg, about 3400 mg, about 3425 mg, about 3450 mg, about 3475 mg, about 3500 mg, about 3525 mg, about 3550 mg, about 3575 mg, about 3600 mg, about 3625 mg, about 3650 mg, about 3675 mg, about 3700 mg, about 3725 mg, about 3750 mg, about 3775 mg, about 3800 mg, about 3825 mg, about 3850 mg, about 3875 mg, about 3900 mg, about 3925 mg, about 3950 mg, about 3975 mg, about 4000 mg, about 4025 mg, about 4050 mg, about 4075 mg, about 4100 mg, about 4125 mg, about 4150 mg, about 4175 mg, about 4200 mg, about 4225 mg, about 4250 mg, about 4275 mg, about 4300 mg, about 4325 mg, about 4350 mg, about 4375 mg, about 4400 mg, about 4425 mg, about 4450 mg, about 4475 mg, about 4500 mg, about 4525 mg, about 4550 mg, about 4575 mg, about 4600 mg, about 4625 mg, about 4650 mg, about 4675 mg, about 4700 mg, about 4725 mg, about 4750 mg, about 4775 mg, about 4800 mg, about 4825 mg, about 4850 mg, about 4875 mg, about 4900 mg, about 4925 mg, about 4950 mg, about 4975 mg, about 5000 mg, about 5025 mg, about 5050 mg, about 5075 mg, about 5100 mg, about 5125 mg, about 5150 mg, about 5175 mg, about 5200 mg, about 5225 mg, about 5250 mg, about 5275 mg, about 5300 mg, about 5325 mg, about 5350 mg, about 5375 mg, about 5400 mg, about 5425 mg, about 5450 mg, about 5475 mg, about 5500 mg, about 5525 mg, about 5550 mg, about 5575 mg, about 5600 mg, about 5625 mg, about 5650 mg, about 5675 mg, about 5700 mg, about 5725 mg, about 5750 mg, about 5775 mg, about 5800 mg, about 5825 mg, about 5850 mg, about 5875 mg, about 5900 mg, about 5925 mg, about 5950 mg, about 5975 mg, about 6000 mg, about 6025 mg, about 6050 mg, about 6075 mg, about 6100 mg, about 6125 mg, about 6150 mg, about 6175 mg, about 6200 mg, about 6225 mg, about 6250 mg, about 6275 mg, about 6300 mg, about 6325 mg, about 6350 mg, about 6375 mg, about 6400 mg, about 6425 mg, about 6450 mg, about 6475 mg, about 6500 mg, about 6525 mg, about 6550 mg, about 6575 mg, about 6600 mg, about 6625 mg, about 6650 mg, about 6675 mg, about 6700 mg, about 6725 mg, about 6750 mg, about 6775 mg, about 6800 mg, about 6825 mg, about 6850 mg, about 6875 mg, about 6900 mg, about 6925 mg, about 6950 mg, about 6975 mg, about 7000 mg, about 7025 mg, about 7050 mg, about 7075 mg, about 7100 mg, about 7125 mg, about 7150 mg, about 7175 mg, about 7200 mg, about 7225 mg, about 7250 mg, about 7275 mg, about 7300 mg, about 7325 mg, about 7350 mg, about 7375 mg, about 7400 mg, about 7425 mg, about 7450 mg, about 7475 mg, about 7500 mg, about 7525 mg, about 7550 mg, about 7575 mg, about 7600 mg, about 7625 mg, about 7650 mg, about 7675 mg, about 7700 mg, about 7725 mg, about 7750 mg, about 7775 mg, about 7800 mg, about 7825 mg, about 7850 mg, about 7875 mg, about 7900 mg, about 7925 mg, about 7950 mg, about 7975 mg, about 8000 mg, about 8025 mg, about 8050 mg, about 8075 mg, about 8100 mg, about 8125 mg, about 8150 mg, about 8175 mg, about 8200 mg, about 8225 mg, about 8250 mg, about 8275 mg, about 8300 mg, about 8325 mg, about 8350 mg, about 8375 mg, about 8400 mg, about 8425 mg, about 8450 mg, about 8475 mg, about 8500 mg, about 8525 mg, about 8550 mg, about 8575 mg, about 8600 mg, about 8625 mg, about 8650 mg, about 8675 mg, about 8700 mg, about 8725 mg, about 8750 mg, about 8775 mg, about 8800 mg, about 8825 mg, about 8850 mg, about 8875 mg, about 8900 mg, about 8925 mg, about 8950 mg, about 8975 mg, about 9000 mg, about 9025 mg, about 9050 mg, about 9075 mg, about 9100 mg, about 9125 mg, about 9150 mg, about 9175 mg, about 9200 mg, about 9225 mg, about 9250 mg, about 9275 mg, about 9300 mg, about 9325 mg, about 9350 mg, about 9375 mg, about 9400 mg, about 9425 mg, about 9450 mg, about 9475 mg, about 9500 mg, about 9525 mg, about 9550 mg, about 9575 mg, about 9600 mg, about 9625 mg, about 9650 mg, about 9675 mg, about 9700 mg, about 9725 mg, about 9750 mg, about 9775 mg, about 9800 mg, about 9825 mg, about 9850 mg, about 9875 mg, about 9900 mg, about 9925 mg, about 9950 mg, about 9975 mg, or about 10,000 mg.

In one embodiment, 15-HEPE present in a composition of the present disclosure comprises at least 90% by weight 15-HEPE. 15-HEPE compositions can comprise even higher purity 15-HEPE, for example at least 95% by weight 15-HEPE or at least 97% by weight 15-HEPE, wherein the 15-HEPE is any form of 15-HEPE as set forth herein. The purity of 15-HEPE can further be defined (e.g. impurity profile) by any of the descriptions of 15-HEPE provided herein.

Above are discussed the amounts of the 15-HEPE in the pharmaceutical composition and their purity. The nature of the essential fatty acids and their synthesis is such that the 15-HEPE composition may include moieties from other essential fatty acids in the essential fatty acid metabolic cascade.

In one embodiment, a composition of the present disclosure contains not more than about 10%, not more than about 9%, not more than about 8%, not more than about 7%, not more than about 6%, not more than about 5%, not more than about 4%, not more than about 3%, not more than about 2%, not more than about 1%, or not more than about 0.5%, by weight of other omega-3 fatty acids including alpha linolenic acid, stearidonic acid, docosahexaenoic acid (DHA) or derivatives thereof. In other embodiments there is substantially no, or no such other omega-3 fatty acids present.

In another embodiment, 15-HEPE represents at least about 60%, at least about 70%, at least about 80%, at least about 90%, at least about 95%, at least about 97%, at least about 98%, at least about 99%, or 100%, by weight, of all fatty acids present in a composition of the present disclosure.

There may be present some residual eicosapentaenoic acid from the synthesis of the 15-HEPE. There may be not more than about 10%, not more than about 9%, not more than about 8%, not more than about 7%, not more than about 6%, not more than about 5%, not more than about 4%, not more than about 3%, not more than about 2%, not more than about 1%, or not more than about 0.5%, by weight EPA. Alternatively, there is substantially no, or no, EPA in a form which has not been modified to the hydroxyl-form.

Additional Active Agents

In one embodiment, the pharmaceutical composition further comprises at least one or more additional active agent(s). In one embodiment, the pharmaceutical composition comprises an amount of the additional active agent that is less than the generally recognized therapeutically effective amount for that agent. In one embodiment, the pharmaceutical composition comprises an amount of the additional active agent that is equal to or greater than the generally recognized therapeutically effective amount for that agent.

In some embodiments, the additional active agent is a hepatitis C virus (HCV) non-antiviral agent, an HCV antiviral agent, a hepatitis B virus (HBV) non-antiviral agent, an HBV antiviral agent, a primary biliary cirrhosis agent, an alcoholic hepatitis agent, a primary sclerosing cholangitis agent, a non-alcoholic steatohepatitis (NASH) agent, an autoimmune hepatitis agent, a pulmonary fibrosis agent, a cystic fibrosis agent, a renal fibrosis agent, a skin fibrosis agent, a myelofibrosis agent, an eosinophilic esophagitis agent, an anti-TGF-β agent, an anti-CTGF agent, a recombinant human serum amyloid P agent, an anti-IL-4 agent, an anti-IL-5 agent (e.g., mepolizumab), an anti-IL-13 agent, a neurochemical receptor agent, an anti-IL-17A agent, a Hh or Hh(R) SMO antagonist, a CCR5 antagonist, a CCR4 cell recruitment inhibitor, a CXCR4 antagonist, an anti-CXCR4 agent, a CXCR3 antagonist, an anti-CCL17 agent, a NOX inhibitor, copaxone, adiponectin, an AMPK agonist, Y-box binding protein-1, a myofibroblast recruitment inhibitor, an anti-Th17 MMP inducer, an anti-extracellular matrix deposition compound, an adenosine receptor antagonist, a microRNA (miR) agent, a stem cell, tenofovir, an anti-collagen crosslinking agent (e.g., simtuzumab, mogamulizumab), or an angiotensin II receptor blocker (ARB) selected from the group consisting of: valsartan, telmisartan, losartan, irbesartan, azilsartan, eprosartan, olmesartan, or a combination of any of the foregoing.

In one embodiment, the one or more additional active agent(s) comprises, consists essentially of, or consists of telmisartan.

In one embodiment, 15-HEPE and one or more active agent(s) are present in a composition of the present disclosure, or are co-administered in a weight ratio of 15-HEPE: additional agent of about 1:1000 to about 1000:1, about 1:500 to about 500:1, about 1:100 to about 100:1, about 1:50 to about 50:1, about 1:25 to about 25:1, about 1:10 to about 10:1, about 1:5 to about 5:1, about 1:4 to about 4:1 about 1:3 to about 3:1, about 1:2 to about 2:1 or about 1:1.

Dosage Forms

A composition for use in accordance with the disclosure can be formulated as one or more dosage units. The terms "dose unit" and "dosage unit" herein refer to a portion of a pharmaceutical composition that contains an amount of a therapeutic agent suitable for a single administration to provide a therapeutic effect. Such dosage units may be administered one to a plurality (i.e. 1 to about 10, 1 to 8, 1 to 6, 1 to 4 or 1 to 2) of times per day, or as many times as needed to elicit a therapeutic response.

In some embodiments, compositions of the present disclosure are in the form of orally deliverable dosage forms or units. Non-limiting examples of suitable dosage forms include tablets (e.g. suspension tablets, bite suspension tablets, rapid dispersion tablets, chewable tablets, etc), caplets, capsules (e.g. a soft or a hard gelatin capsule or HPMC capsule), lozenges, sachets, cachets, troches, pellets, suspension, elixirs, syrups or any other solid dosage form reasonably adapted for oral administration. The terms "oral delivery" and "oral administration" herein include any form of delivery wherein the agent or composition is placed in the mouth of the subject under treatment, whether swallowed or not. This therefore includes buccal and sublingual administration, as well as esophagael administration.

Alternatively, compositions of the present disclosure can also be formulated for rectal, topical, or parenteral (e.g. subcutaneous, intramuscular, intravenous and intradermal or infusion) delivery.

In discussing the amount of 15-HEPE in a composition of the present disclosure, this may be split over several dosage forms. There is a limit as to the size for oral administration. If a subject is to be administered 1 to 4 g 15-HEPE a day, this may be by up to 4 capsules, each providing 1 g 15-HEPE.

Compositions of the present disclosure can be in the form of liquid dosage forms or dose units to be imbibed directly or they can be mixed with food or beverage prior to ingestion. Non-limiting examples of suitable liquid dosage forms include solutions, suspensions, elixirs, syrups, liquid aerosol formulations, and the like.

In another embodiment, compositions of the present disclosure comprise one or more pharmaceutically acceptable excipients. The term "pharmaceutically acceptable excipient" herein means any substance, not itself a therapeutic agent, used as a carrier or vehicle for delivery of a therapeutic agent to a subject or added to a pharmaceutical composition to improve its handling or storage properties or to permit or facilitate formation of a unit dose of the composition, and that does not produce unacceptable toxicity or interaction with other components in the composition. By way of example only, a pharmaceutical composition according to the present disclosure may comprise one or more of: antioxidants, surfactants, preservatives, flavouring agents, co-solvents, viscosity aids, suspension aids, and lipophilic phases.

In one embodiment, the pharmaceutical composition comprises one or more antioxidants such as ascorbic acid, palmitic acid, ascorbyl palmitate, α-tocopherol, idebenone, ubiquinone, ferulic acid, coenzyme Q10, lycopene, green tea; catechins; epigallocatechin 3-gallate (EGCG), green tea polyphenols (GTP), silymarin, coffeeberry, resveratrol, grape seed, pomegranate extracts, genisten, pycnogenol, niacinamide, butylated hydroxyltoluene (BHT), butylated hydroxylanisol (BHA), and the like. In one embodiment, the pharmaceutical composition comprises about 0.01 wt. % to about 2 wt. % of an antioxidant, for example about 0.01 wt. %, about 0.02 wt. %, about 0.03 wt. %; about 0.04 wt. %, about 0.05 wt. %, about 0.06 wt. %, about 0.07 wt. %, about 008 wt. %, about 0.09 wt. %, about 0.1 wt. %, about 0.11 wt. %, about 0.12 wt. %, about 0.13 wt. %, about 0.14 wt. %, about 0.15 wt. %, about 0.16 wt. %, about 0.17 wt. %, about 0.18 wt. %, about 0.19 wt. %, about 0.2 wt. %, about 0.21 wt. %, about 0.22 wt. %, about 0.23 wt. %, about 0.24 wt. %, about 0.25 wt. %, about 0.26 wt. %, about 0.27 wt. %, about 0.28 wt. %, about 0.29 wt. %, about 0.3 wt. %, about 0.31 wt. %, about 0.32 wt. %, about 0.33 wt. %, about 0.34 wt. %, about 0.35 wt. %, about 0.36 wt. %, about 0.37 wt.

%, about 0.38 wt. %, about 0.39 wt. %, about 0.4 wt. %, about 0.41 wt. %, about 0.42 wt. %, about 0.43 wt. %, about 0.44 wt. %, about 0.45 wt. %, about 0.46 wt. %, about 0.47 wt. %, about 0.48 wt. %, about 0.49 wt. %, about 0.5 wt. %, about 0.51 wt. %, about 0.52 wt. %, about 0.53 wt. %, about 0.54 wt. %, about 0.55 wt. %, about 0.56 wt. %, about 0.57 wt. %, about 0.58 wt. %, about 0.59 wt. %, about 0.6 wt. %, about 0.61 wt. %, about 0.62 wt. %, about 0.63 wt. %, about 0.64 wt. %, about 0.65 wt. %, about 0.66 wt. %, about 0.67 wt. %, about 0.68 wt. %, about 0.69 wt. %, about 0.7 wt. %, about 0.71 wt. %, about 0.72 wt. %, about 0.73 wt. %, about 0.74 wt. %, about 0.75 wt. %, about 0.76 wt. %, about 0.77 wt. %, about 0.78 wt. %, about 0.79 wt. %, about 0.8 wt. %, about 0.81 wt. %, about 0.82 wt. %, about 0.83 wt. %, about 0.84 wt. %, about 0.85 wt. %, about 0.86 wt. %, about 0.87 wt. %, about 0.88 wt. %, about 0.89 wt. %, about 0.9 wt. %, about 0.91 wt. %, about 0.92 wt. %, about 0.93 wt. %, about 0.94 wt. %, about 0.95 wt. %, about 0.96 wt. %, about 0.97 wt. %, about 0.98 wt. %, about 0.99 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, or about 2 wt. % of the one or more antioxidant.

Therapeutic Methods

The compositions and formulations disclosed herein may be used in the treatment of fibrosis. In one embodiment the fibrosis is associated with an organ or tissue associated with a lung, a liver, a heart, a kidney, one or more eyes, mediastinum, bone marrow, retroperitoneaum, skin, an intestine, a joint, a reproductive organ, or a combination thereof. In some embodiments, the fibrosis is associated with liver tissue. In one embodiment, the fibrosis comprises idiopathic pulmonary fibrosis.

In some embodiments, the fibrosis is associated with non-alcoholic fatty liver disease (NAFLD). In some embodiments, an NAFLD activity score (NAS) is reduced in the subject after administration of the composition. In some embodiments, the NAS is reduced in the subject compared to baseline. In some embodiments, the NAS is reduced in comparison to a second subject who has not been administered the composition. In some embodiments, the second subject has been administered a placebo. In some embodiments, the second subject is on fibrosis therapy.

In some embodiments, the subject is on fibrosis therapy. In some embodiments, the fibrosis therapy is continued during administration of the composition. In other embodiments, the fibrosis therapy is discontinued during administration of the composition. For example, in some embodiments the subject is on telmisartan therapy and, after commencing a therapeutic method comprising administration of a composition comprising 15-HEPE as disclosed herein, the telmisartan therapy is discontinued.

In some embodiments, the composition is orally administered.

In some embodiments, the 15-HEPE is the only active ingredient in the composition. In other embodiments, the composition further comprises an additional agent for affecting the fibrosis therapy.

In some embodiments, the present disclosure provides a method of treating fibrosis in a subject on fibrosis therapy, the method comprising administering to the subject a composition comprising 15-HEPE. In some embodiments, the fibrosis is associated with an organ or tissue selected from the group consisting of: lung, liver, heart, kidney, eye, mediastinum, bone marrow, retroperitoneaum, skin, intestine, joint, a reproductive organ, and a combination thereof. In some embodiments, the fibrosis is liver fibrosis. In some embodiments, the fibrosis is associated with non-alcoholic fatty liver disease (NAFLD). In some embodiments, an NAFLD activity score (NAS) is reduced in the subject after administration of the composition. In some embodiments, the NAS is reduced in the subject compared to baseline. In some embodiments, the NAS is reduced in comparison to a second subject who has not been administered the composition. In some embodiments, the second subject has been administered a placebo. In some embodiments, the second subject is on fibrosis therapy. In some embodiments, the fibrosis therapy comprises administration of an HCV non-antiviral agent, an HCV antiviral agent, an HBV non-antiviral agent, an HBV antiviral agent, a primary biliary cirrhosis agent, an alcoholic hepatitis agent, a primary sclerosing cholangitis agent, a NASH agent, an autoimmune hepatitis agent, a pulmonary fibrosis agent, a cystic fibrosis agent, a renal fibrosis agent, a skin fibrosis agent, a myelofibrosis agent, an eosinophilic esophagitis agent, an anti-TGF-β agent, an anti-CTGF agent, a recombinant human serum amyloid P agent, an anti-IL-4 agent, an anti-IL-5 agent (e.g., mepolizumab), an anti-IL-13 agent, a neurochemical receptor agent, an anti-IL-17A agent, a Hh or Hh(R) SMO antagonist, a CCR5 antagonist, a CCR4 cell recruitment inhibitor, a CXCR4 antagonist, an anti-CXCR4 agent, a CXCR3 antagonist, an anti-CCL17 agent, a NOX inhibitor, copaxone, adiponectin, an AMPK agonist, Y-box binding protein-1, a myofibroblast recruitment inhibitor, an anti-Th17 MMP inducer, an anti-extracellular matrix deposition compound, an adenosine receptor antagonist, a micro-RNA (miR) agent, a stem cell, tenofovir, an anti-collagen crosslinking agent (e.g., simtuzumab, mogamulizumab), or an angiotensin H receptor blocker (ARB) selected from the group consisting of: valsartan, telmisartan, losartan, irbesartan, azilsartan, eprosartan, olmesartan, or a combination of any of the foregoing. In some embodiments, the subject is on fibrosis therapy. In some embodiments, the fibrosis therapy is continued during administration of the composition. In some embodiments, the second subject is on fibrosis therapy. In some embodiments, the composition is orally administered.

In some embodiments of the methods disclosed herein, the 15-HEPE is the only active ingredient in the composition. In some embodiments, the composition further comprises an additional agent for affecting the fibrosis therapy.

In some embodiments, the method further comprises identifying the subject as having fibrosis before administering the composition comprising 15-HEPE. In some embodiments, the method further comprises identifying the subject as having an increased risk of developing fibrosis before administering the composition comprising 15-HEPE. In some embodiments, the step of identifying comprises determining a NAS associated with the subject. In some embodiments, the NAS associated with the subject is at least 3. In some embodiments, the step of identifying comprises screening for a genetic mutation in a nucleic acid molecule associated with the subject. In some embodiments, the step of identifying comprises obtaining an analysis of blood and/or serum associated with the subject. In some embodiments, the step of identifying comprises examining a tissue associated with the subject. In some embodiments, the step of examining comprises analyzing a histological tissue sample (e.g., a biopsy) associated with the subject.

In some embodiments, methods of the present disclosure cause a NAS value to decrease in a subject. In some embodiments, the method further comprises determining a second, lower NAS value associated with the subject after administering the composition for a period of time.

In one embodiment, the method comprises administering a pharmaceutical composition as disclosed herein to a subject once per day, twice per day, three times per day, or more than three times per day.

In one embodiment, the invention provides use of 15-HEPE or a composition comprising 15-HEPE to treat or prevent fibrosis in a subject in need thereof and optionally wherein any one or more of (a) through (m) is true:

(a) the fibrosis is associated with an organ or tissue selected from the group consisting of: lung, liver, heart, mediastinum, bone marrow, retroperitoneaum, skin, intestine, joint, a reproductive organ, and a combination thereof;

(b) the fibrosis is liver fibrosis or idiopathic pulmonary fibrosis;

(c) the fibrosis is associated with non-alcoholic fatty liver disease (NAFLD);

(d) the NAFLD activity score (NAS) is reduced in the subject after administration of the composition;

(e) the NAS is reduced in the subject compared to baseline;

(f) the NAS is reduced in comparison to a second subject who has not been administered the composition and/or the second subject has been administered a placebo;

(g) the subject is on fibrosis therapy;

(h) the fibrosis therapy is continued during administration of the composition;

(i) the 15-HEPE or the composition is orally administered;

(j) the 15-HEPE is in free acid form;

(k) the 15-HEPE is in esterified form;

(l) the esterified form is an alkyl ester or triglyceride form;

(m) the 15-HEPE is in salt form;

(n) the 15-HEPE comprises 15(S)-HEPE; and/or (o) the 15-HEPE comprises 15(R)-HEPE.

Unless otherwise defined, all technical and scientific terms used herein have the same meaning as commonly understood by one of ordinary skill in the art to which this present disclosure pertains. Although methods and materials similar or equivalent to those described herein can be used in the practice of the present disclosure, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

While the present disclosure is capable of being embodied in various forms, the present description below of several embodiments is made with the understanding that the present disclosure is to be considered as an exemplification of the present disclosure, and is not intended to limit the technology disclosed herein to the specific embodiments illustrated. Headings are provided for convenience only and are not to be construed to limit the technology disclosed herein in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." In this manner, slight variations from a stated value can be used to achieve substantially the same results as the stated value. Also, the disclosure of ranges is intended as a continuous range including every value between the minimum and maximum values recited as well as any ranges that can be formed by such values. Also disclosed herein are any and all ratios (and ranges of any such ratios) that can be formed by dividing a recited numeric value into any other recited numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present disclosure.

As used herein, "treating" or "treatment" of a disease, disorder, or condition includes at least partially: (1) preventing the disease, disorder, or condition, i.e. causing the clinical symptoms of the disease, disorder, or condition not to develop in a mammal that is exposed to or predisposed to the disease, disorder, or condition but does not yet experience or display symptoms of the disease, disorder, or condition; (2) inhibiting the disease, disorder, or condition, i.e., arresting or reducing the development of the disease, disorder, or condition or its clinical symptoms; or (3) relieving the disease, disorder, or condition. i.e., causing regression of the disease, disorder, or condition or its clinical symptoms. The term "prevention" in relation to a given disease or disorder means: preventing the onset of disease development if none had occurred, preventing the disease or disorder from occurring in a subject that may be predisposed to the disorder or disease but has not yet been diagnosed as having the disorder or disease, and/or preventing further disease/disorder development if already present.

An "effective amount," as used herein, refers to the amount of an active composition that is required to confer a therapeutic effect on the subject. A "therapeutically effective amount," as used herein, refers to a sufficient amount of an agent or a compound being administered which will relieve to some extent one or more of the symptoms of the disease, disorder, or condition being treated. In some embodiments, the result is a reduction and/or alleviation of the signs, symptoms, or causes of a disease, or any other desired alteration of a biological system. For example, in some embodiments, an "effective amount" for therapeutic uses is the amount of the composition including a compound as disclosed herein required to provide a clinically significant decrease in disease symptoms without undue adverse side effects. In some embodiments, an appropriate "effective amount" in any individual case is determined using techniques, such as a dose escalation study. The term "therapeutically effective amount" includes, for example, a prophylactically effective amount. In other embodiments, an "effective amount" of a compound disclosed herein, such as a compound of Formula (A) or Formula (I), is an amount effective to achieve a desired pharmacologic effect or therapeutic improvement without undue adverse side effects. In other embodiments, it is understood that "an effect amount" or "a therapeutically effective amount" varies from subject to subject, due to variation in metabolism, age, weight, general condition of the subject, the condition being treated, the severity of the condition being treated, and the judgment of the prescribing physician. The term "pharmaceutically acceptable" in the present context means that the substance in question does not produce unacceptable toxicity to the subject or interaction with other components of the composition.

Without further description, it is believed that one of ordinary skill in the art may, using the preceding description and the following illustrative examples, make and utilize the agents of the present disclosure and practice the claimed methods. The following working examples are provided to facilitate the practice of the present disclosure, and are not to be construed as limiting in any way the remainder of the disclosure.

EXAMPLES

Example 1

The purpose of this study was to examine the effects of 15-HEPE and 15-HETrE compared to vehicle and to telmisartan in a mouse model of NAFLD.

Protocol

C57/BL6 mice obtained from Charles River Laboratories were divided into 6 study groups as follows:

Group 1 (Vehicle): Twelve mice were each administered a single dose of steptozotocin after birth and fed a high-fat diet for four weeks. The mice were then fed vehicle in a volume of 10 mL/kg once daily from 5 to 12 weeks of age.

Group 2 (telmisartan): Twelve mice were each administered a single dose of steptozotocin after birth and fed a high-fat diet for four weeks. The mice were then fed telmisartan in an amount of 5 mg/kg once daily from 5 to 12 weeks of age.

Group 3 (15-HEPE, low dose): Twelve mice were each administered a single dose of steptozotocin after birth and fed a high-fat diet for four weeks. The mice were then fed 15-HEPE in an amount of 50 mg/kg once daily from 5 to 12 weeks of age.

Group 4 (15-HEPE, high dose): Twelve mice were each administered a single dose of steptozotocin after birth and fed a high-fat diet for four weeks. The mice were then fed 15-HEPE in an amount of 500 mg/kg once daily from 5 to 12 weeks of age.

Group 5 (15-HETrE, low dose): Twelve mice were each administered a single dose of steptozotocin after birth and fed a high-fat diet for four weeks. The mice were then fed 15-HETrE in an amount of 10 mg/kg once daily from 5 to 12 weeks of age.

Group 6 (15-HETrE, high dose): Twelve mice were administered a single dose of steptozotocin after birth and fed a high-fat diet for four weeks. The mice were then fed 15-HETrE in an amount of 100 mg/kg once daily from 5 to 12 weeks of age.

At 12 weeks of age, all mice were assessed for changes in:
serum biochemistry (e.g., ALT levels, LDL levels, VLDL levels, HDL levels, triglyceride levels, total cholesterol level),
fibrosis (e.g., histology using sirius red staining), and
NAFLD activity score (including, e.g., H&E staining histology).

Results

Figure 2:
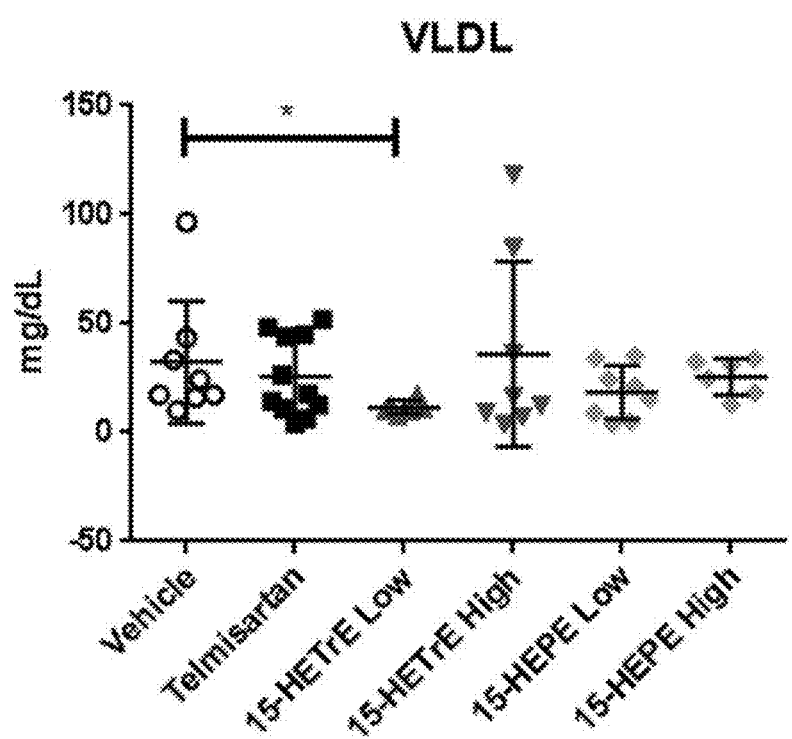
FIG. 2 shows differences in very low density lipoprotein (VLDL) levels for mice given a single dose of steptozotocin after birth, fed a high-fat diet for 4 weeks, then treated for 8 weeks with vehicle, telmisartan, 15-HETrE, or 15-HEPE.
Figure 3:
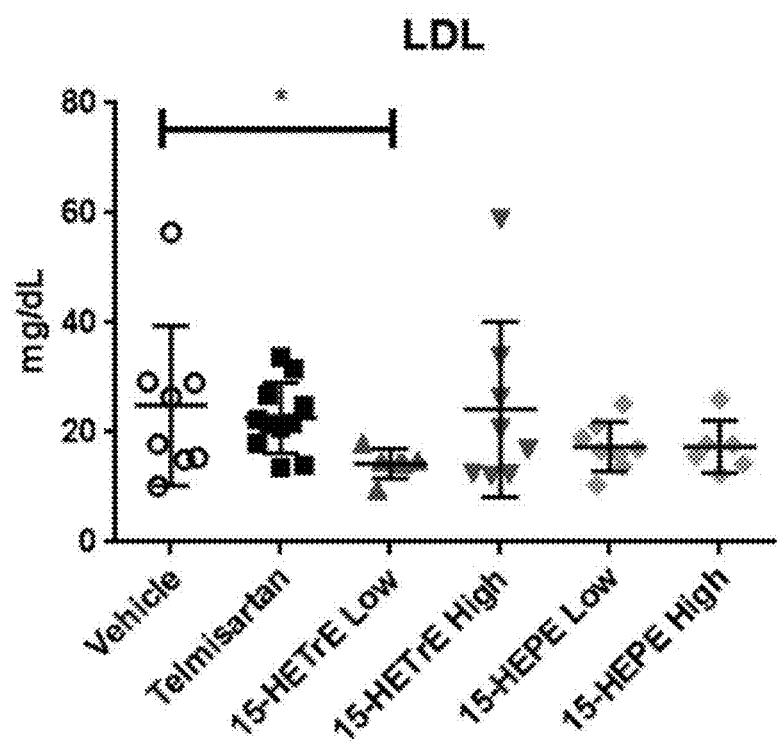
FIG. 3 shows differences in low density lipoprotein (LDL) levels for mice given a single dose of steptozotocin after birth, fed a high-fat diet for 4 weeks, then treated for 8 weeks with vehicle, telmisartan, 15-HETrE, or 15-HEPE
Figure 4:
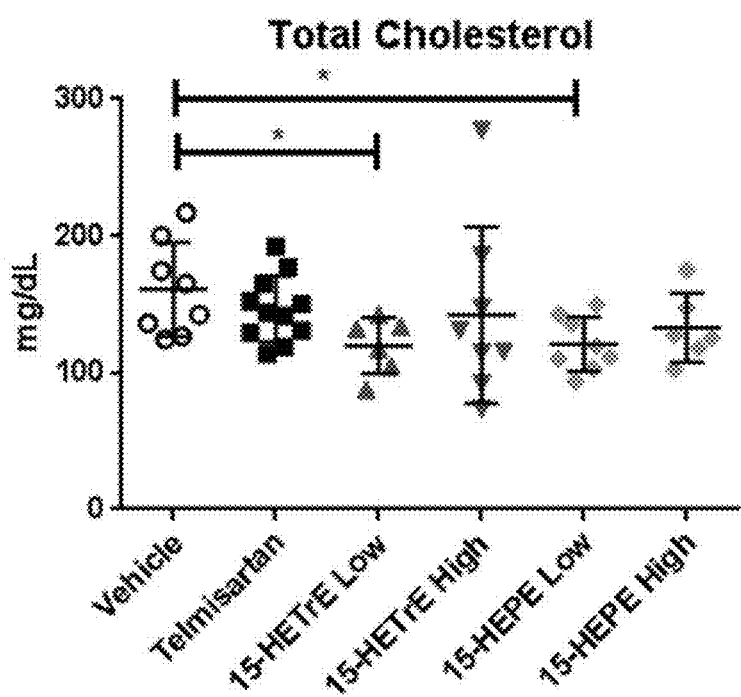
FIG. 4 shows differences in total cholesterol levels for mice given a single dose of steptozotocin after birth, fed a high-fat diet for 4 weeks, then treated for 8 weeks with vehicle, telmisartan, 15-HETrE, or 15-HEPE.
Figure 5:
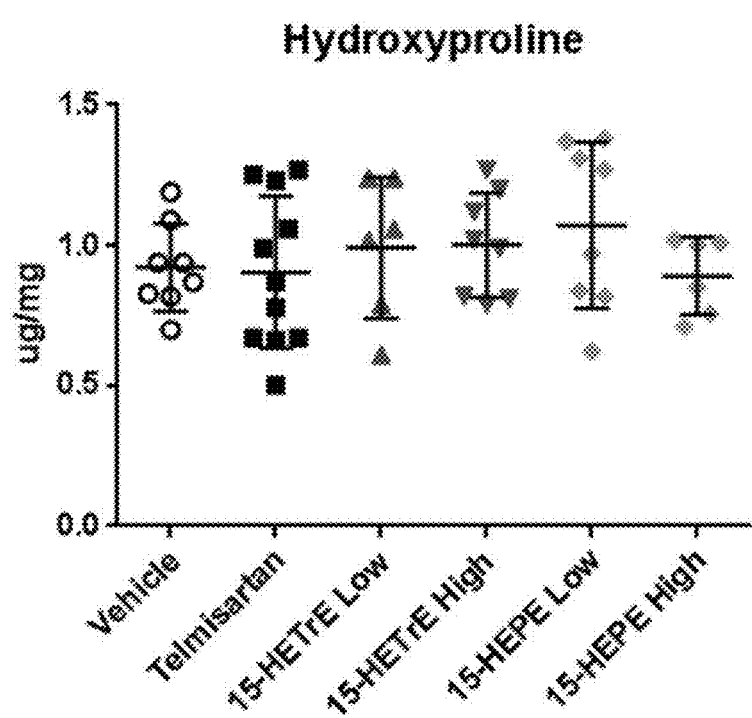
FIG. 5 shows differences in hydroxyproline levels for mice given a single dose of steptozotocin after birth, fed a high-fat diet for 4 weeks, then treated for 8 weeks with vehicle, telmisartan, 15-HETrE, or 15-HEPE.
Figure 6:
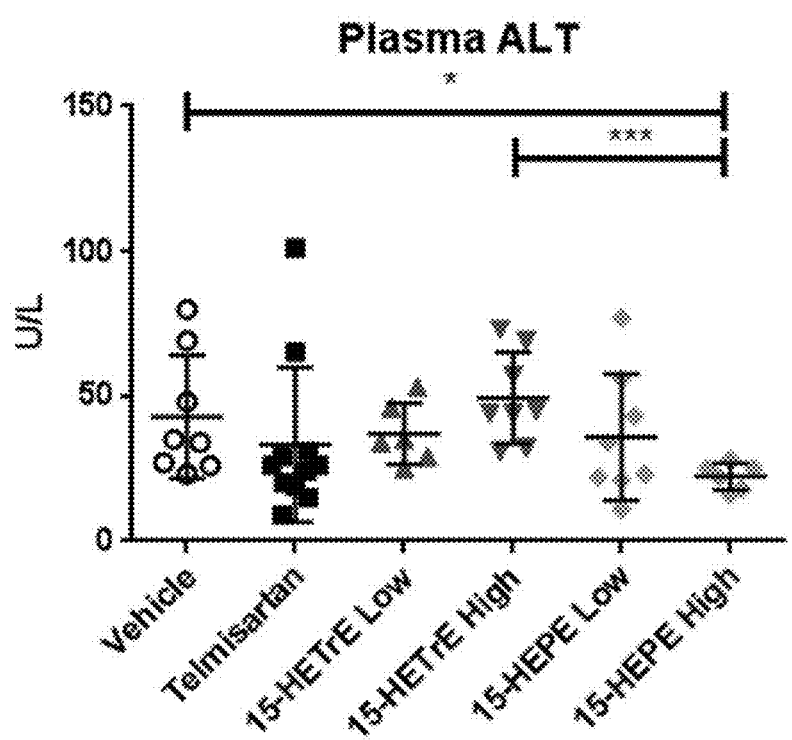
FIG. 6 shows differences in plasma alanine transaminase (ALT) levels for mice given a single dose of steptozotocin after birth, fed a high-fat diet for 4 weeks, then treated for 8 weeks with vehicle, telmisartan, 15-HETrE, or 15-HEPE.
Figure 7A:
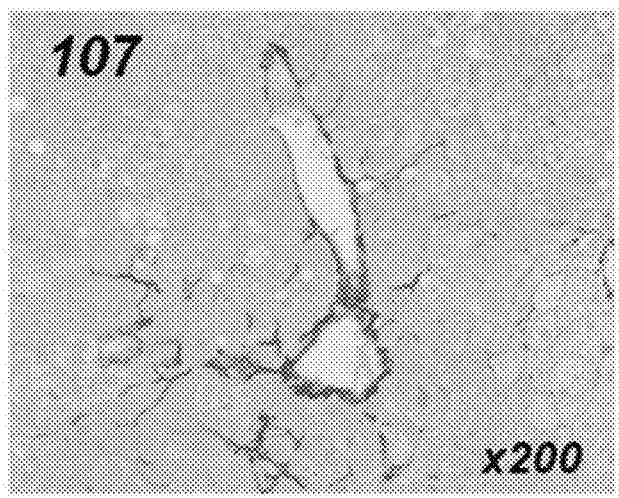
FIG. 7A shows histology (sirius red staining, 200×) showing collagen formation in mice given a single dose of steptozotocin after birth, fed a high-fat diet for 4 weeks, then treated for 8 weeks with vehicle.
Figure 7B:
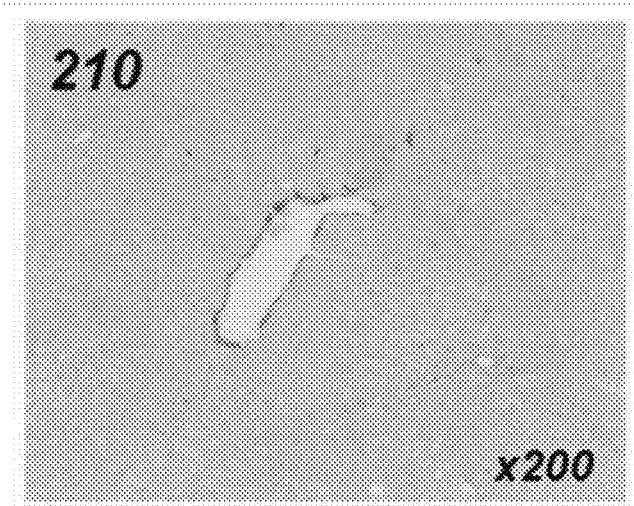
FIG. 7B shows histology (sirius red staining, 200×) showing collagen formation in mice given a single dose of steptozotocin after birth, fed a high-fat diet for 4 weeks, then treated for 8 weeks with telmisartan.
Figure 7C:
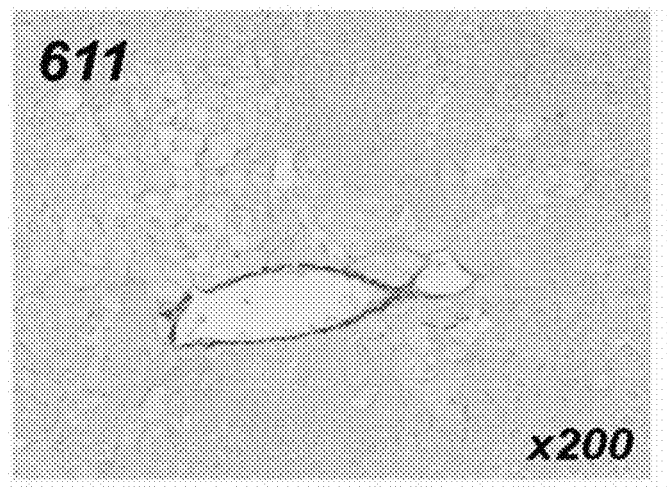
FIG. 7C shows histology (sirius red staining, 200×) showing collagen formation in mice given a single dose of steptozotocin after birth, fed a high-fat diet for 4 weeks, then treated for 8 weeks with 15-HEPE.
Figure 7D:
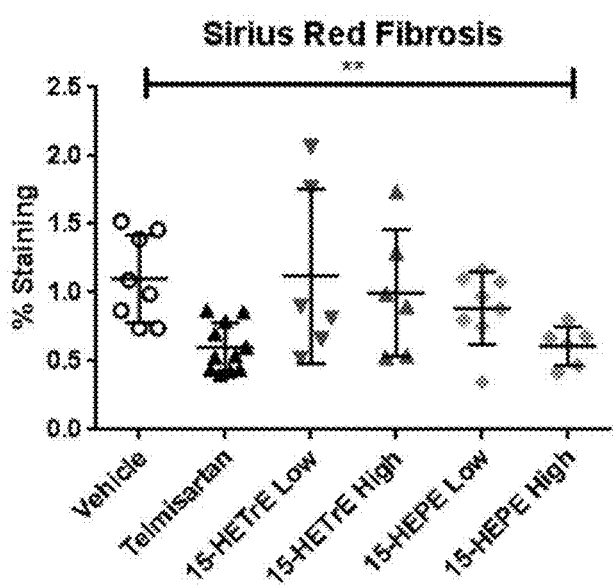
FIG. 7D graphically shows the degree of sirius red staining observed in the histology samples of FIGS. 7A-7C.

As shown in FIG. 1, serum triglycerides were significantly lower (Mann Whitney) for the low-dose 15-HETrE group than vehicle. Similarly, VLDL and LDL levels were significantly lower in the low-dose 15-HETrE group compared to vehicle (FIGS. 2-3). Total cholesterol levels were significantly lower in the low-dose 15-HETrE and the low-dose 15-HEPE groups compared to vehicle (FIG. 4). Hydroxyproline levels were not significantly different in any group compared to vehicle, as shown in FIG. 5. As shown in FIG. 6, plasma ALT levels were significantly lower in the high-dose 15-HEPE group compared to vehicle and compared to the high-dose 15-HETrE group. Notably, the telmaisartan group did not show statistically significant reductions in serum triglycerides, VLDL, LDL, total cholesterol, hydroxyproline, or plasma ALT compared to vehicle.

Histological results (sirius red staining) are shown in FIGS. 7A-7D, and reveal that the high-dose 15-HEPE group developed a statistically equivalent low amount of fibrosis as the telmisartan compared to vehicle.

Figure 8A:
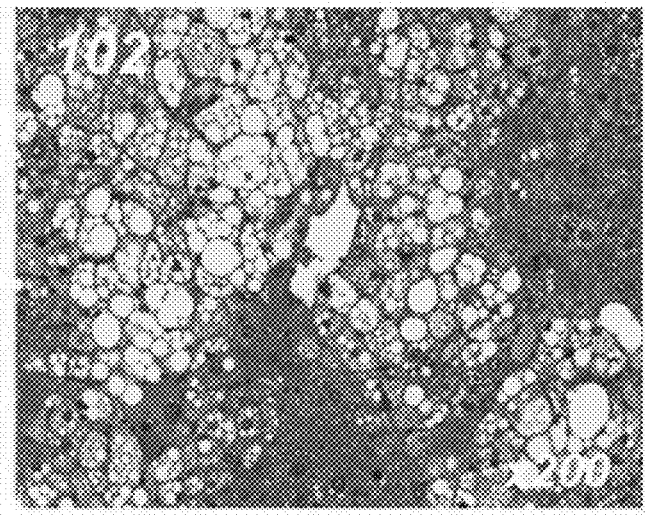
FIG. 8A shows histology (hematoxylin and eosin staining, 200×) of liver tissues obtained from mice given a single dose of steptozotocin after birth, fed a high-fat diet for 4 weeks, then treated for 8 weeks with vehicle.
Figure 8B:
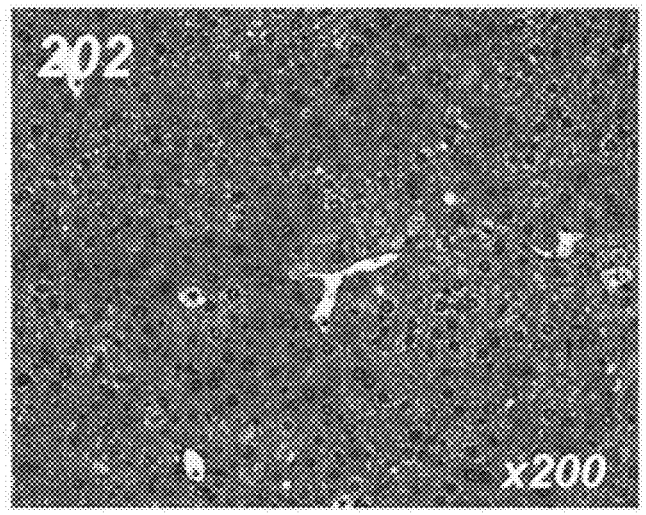
FIG. 8B shows histology (hematoxylin and eosin staining, 200×) of liver tissues obtained from mice given a single dose of steptozotocin after birth, fed a high-fat diet for 4 weeks, then treated for 8 weeks with telmisartan.
Figure 8C:
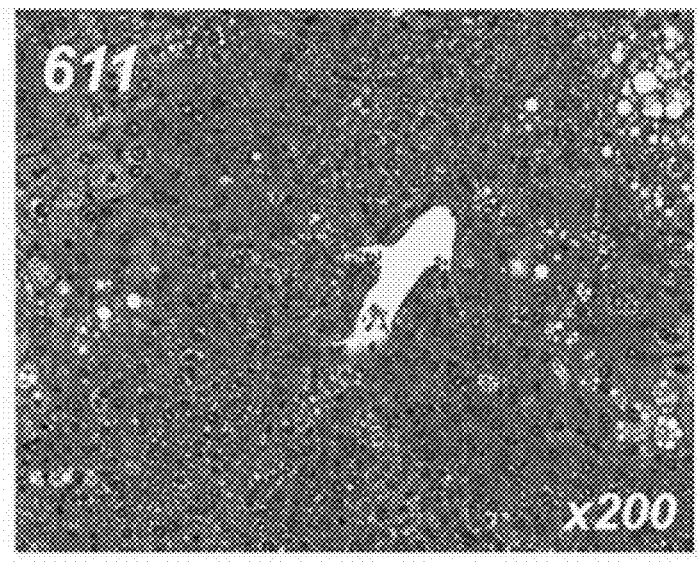
FIG. 8C shows histology (hematoxylin and eosin staining, 200×) of liver tissues obtained from mice given a single dose of steptozotocin after birth, fed a high-fat diet for 4 weeks, then treated for 8 weeks with 15-HEPE.
Figure 8D:
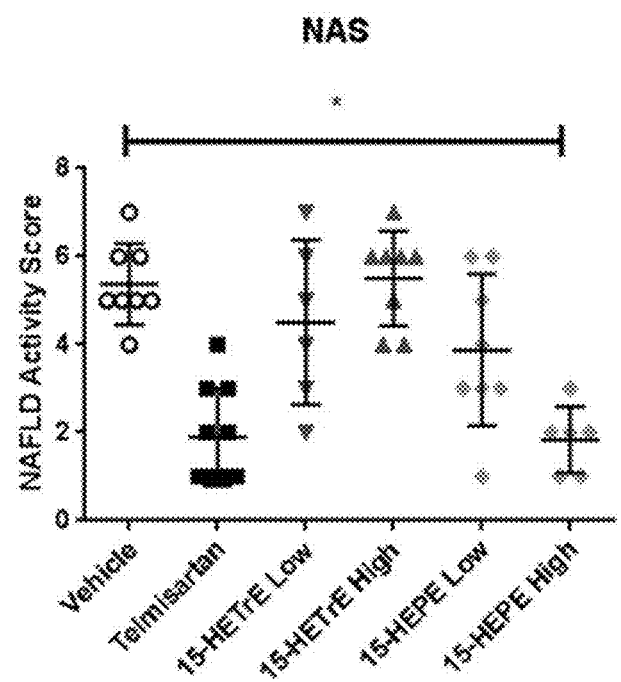
FIG. 8D shows NAFLD Activity Scores (NAS) for mice given a single dose of steptozotocin after birth, fed a high-fat diet for 4 weeks, then treated for 8 weeks with vehicle, telmisartan, 15-HETrE (low or high dose), or 15-HEPE (low or high dose).

As revealed in FIGS. 8A-D, mice in the high-dose 15-HEPE group (FIG. 8C) showed significantly lower NAS (p<0.01) than placebo (FIG. 8A). The telmisartan group (FIG. 8B) also showed significantly lower NAS (p<0.001) vs. vehicle.

Example 2

Non-alcoholic steatohepatitis (NASH) was induced in mice by a single subcutaneous injection of 200 µg of streptozotocin (Sigma Aldrich) two days after birth and feeding with high fat diet (57 kcal % fat, CLEA Japan) after 4 weeks of age. After randomization, each mouse was orally administered vehicle, telmisartan (10 mg/kg), 15-HEPE (500 mg/kg) or EPA (500 mg/kg) once daily from 5 to 9 weeks of age. At the end of the 9th week, the mice were sacrificed and analyzed.

Figure 9:
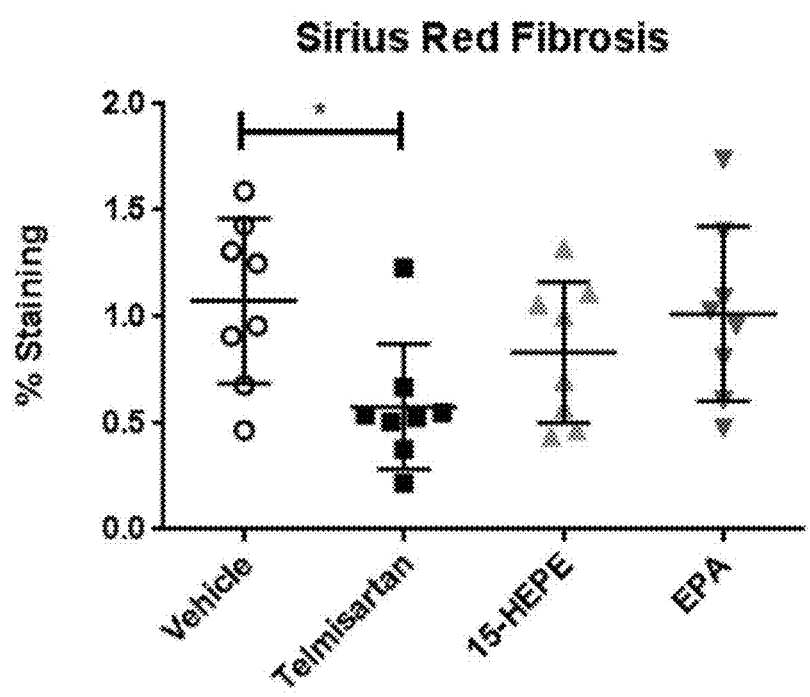
FIG. 9 shows effects of 15-HEPE compared to vehicle, telmisartan and EPA after 4 weeks in a mouse model.

As shown in FIG. 9, 15-HEPE (500 mg/kg) was more effective at treating and/or preventing liver fibrosis in a mouse model than EPA (500 mg/kg) or vehicle (FIG. 9).

Example 3

Figure 10:
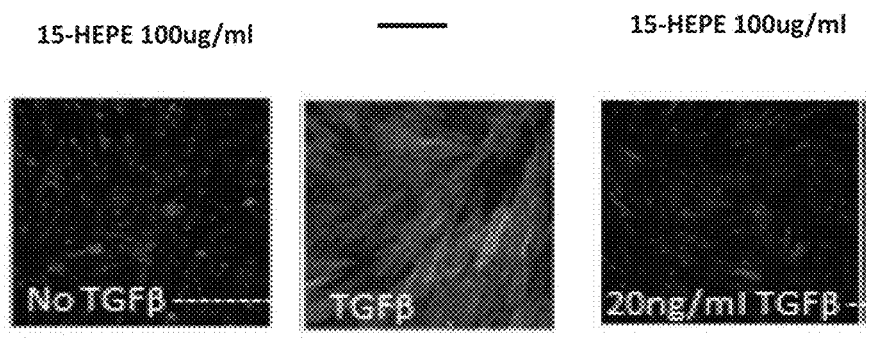
FIG. 10 shows inhibition of TGF-beta induced alpha-SMA production by As 15-HEPE at 100 ug/ml.

Lung Fibroblasts from Idiopathic Pulmonary Fibrosis (IPF) patients were plated at 10000 cells per well in their respective growth mediums and allowed to attach overnight. After attachment, the cells were pretreated with 15(S)-HEPE for 2 hours in their respective assay mediums. After 2 hours, the cells were then treated with compounds+/−TGF beta (20 ng/ml) for 48 hours. After 48 hours, the conditioned media was collected and frozen at −80° C. for future collagen analysis. After collection, the cells were stained for SMA I expression. The collagen ELISA was performed according to the manufacturer's instructions. As shown in FIG. 10, 15-HEPE at 100 ug/ml inhibited TGF-beta induced alpha-SMA production. No cytotoxicity was observed.

Example 4

Figure 11:
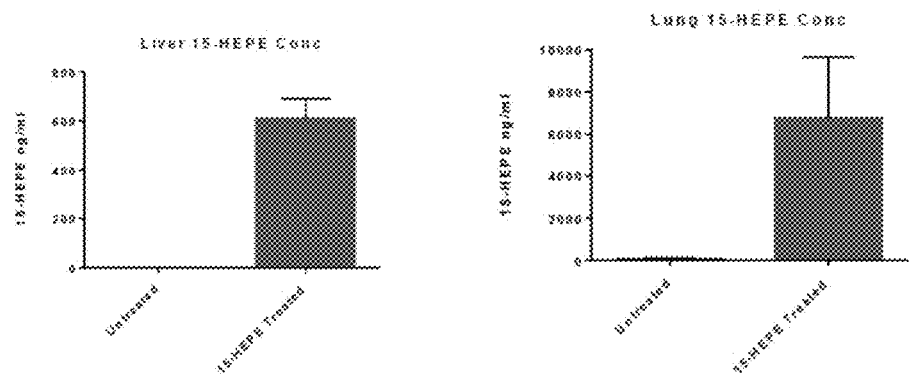
FIG. 11 shows liver and lung 15-HEPE concentration in animals dosed with 15-HEPE (DS102) 500 mg/kg for 7 days versus untreated animals.

Rats (n=5) were dosed with 15-HEPE (DS102) 500 mg/kg for 7 days and organs excised to analyse 15-HEPE levels in the tissues of treated vs untreated animals. As shown in FIG. 11, there was significantly more 15-HEPE in the liver and lung as of treated animals as compared to untreated control.

What is claimed is:

1. A method of reducing or preventing fibrosis in a subject in need thereof, the method comprising;
identifying the subject as having or as having an increased risk for developing fibrosis associated with an organ or tissue selected from the group consisting of: liver, heart, mediastinum, bone marrow, retroperitoneaum, skin, intestine, joint, and a reproductive organ, or a combination thereof; and, based on the identification,
administering to the subject a composition comprising 15-HEPE wherein the 15-HEPE represents at least 80% by weight of all fatty acids in the pharmaceutical composition.

2. The method of claim 1, wherein the fibrosis is liver fibrosis.

3. The method of claim 1, wherein the fibrosis is associated with non-alcoholic fatty liver disease (NAFLD).

4. The method of claim 3, wherein a NAFLD activity score (NAS) is reduced in the subject after administration of the composition.

5. The method of claim 4, wherein the NAS is reduced in the subject compared to baseline.

6. The method of claim 4, wherein the NAS is reduced in comparison to a second subject who has not been administered the composition.

7. The method of claim 6, wherein the second subject has been administered a placebo.

8. The method of claim 6, wherein the second subject is on fibrosis therapy.

9. The method of claim 8, wherein the fibrosis therapy comprises administration of a hepatitis C virus (HCV) non-antiviral agent, an HCV antiviral agent, a hepatitis B virus (HBV) non-antiviral agent, an HBV antiviral agent, a primary biliary cirrhosis agent, an alcoholic hepatitis agent, a primary sclerosing cholangitis agent, a NASH agent, an autoimmune hepatitis agent, a pulmonary fibrosis agent, a cystic fibrosis agent, a renal fibrosis agent, a skin fibrosis agent, a myelofibrosis agent, an eosinophilic esophagitis agent, an anti-TGF-β agent, an anti-CTGF agent, a recombinant human serum amyloid P agent, an anti-IL-4 agent, an anti-IL-5 agent (e.g., mepolizumab), an anti-IL-13 agent, a neurochemical receptor agent, an anti-IL-17A agent, a Hh or Hh(R) SMO antagonist, a CCR5 antagonist, a CCR4 cell recruitment inhibitor, a CXCR4 antagonist, an anti-CXCR4 agent, a CXCR3 antagonist, an anti-CCL17 agent, a NOX inhibitor, copaxone, adiponectin, an AMPK agonist, Y-box binding protein-1, a myofibroblast recruitment inhibitor, an anti-Th17 MMP inducer, an anti-extracellular matrix deposition compound, an adenosine receptor antagonist, a micro-RNA (miR) agent, a stem cell, tenofovir, an anti-collagen crosslinking agent (e.g., simtuzumab, mogamulizumab), or an angiotensin II receptor blocker (ARB) selected from the group consisting of: valsartan, telmisartan, losartan, irbesartan, azilsartan, eprosartan, olmesartan, or a combination of any of the foregoing.

10. The method of claim 1, wherein the subject is on fibrosis therapy.

11. The method of claim 10, wherein the fibrosis therapy is continued during administration of the 15-HEPE or the composition.

12. The method of claim 1, wherein the 15-HEPE or the composition is orally administered.

13. The method of claim 1, wherein the 15-HEPE is in free acid form.

14. The method of claim 1, wherein the 15-HEPE is in esterified form.

15. The method of claim 14, wherein the esterified form is an alkyl ester form.

16. The method of claim 14, wherein the esterified form is a triglyceride form.

17. The method of claim 1, wherein the 15-HEPE is in salt form.

18. The method of claim 1, wherein the 15-HEPE comprises 15(S)-HEPE.

19. The method of claim 1, wherein the 15-HEPE comprises 15(R)-HEPE.

* * * * *